(12) United States Patent
Sakura, Jr.

(10) Patent No.: US 7,942,841 B2
(45) Date of Patent: May 17, 2011

(54) EXSANGUNATION DEVICE AND METHOD (76) Inventor: Chester Y. Sakura, Jr., Albuquerque, NM (US)

( * ) Notice: Subject to any disclaimer, the term of this patent is extended or adjusted under 35 U.S.C. 154(b) by 1125 days.

(21) Appl. No.: 11/569,296

(22) PCT Filed: May 19, 2005

(86) PCT No.: PCT/US2005/017591
§ 371 (c)(1),
(2), (4) Date: Nov. 17, 2006

(87) PCT Pub. No.: WO2005/112841
PCT Pub. Date: Dec. 1, 2005

(65) Prior Publication Data
US 2007/0219472 A1    Sep. 20, 2007

Related U.S. Application Data (63) Continuation-in-part of application No. 10/848,692, filed on May 19, 2004, now abandoned.

(51) Int. Cl.
A61F 5/37    (2006.01)
(52) U.S. Cl. .......................................................... 602/21
(58) Field of Classification Search .................... 602/21, 602/22, 48, 62, 64; 606/201–204.55; 128/878, 128/879, 880, 898
See application file for complete search history.

(56) References Cited

U.S. PATENT DOCUMENTS

| | | | |
|---|---|---|---|
| 1,862,026 A | 6/1932 | Levison | |
| 3,525,340 A | 8/1970 | Glbert | |
| 3,971,374 A | 7/1976 | Wagner | |
| 4,192,300 A | 3/1980 | Devers | |
| 4,733,659 A | 3/1988 | Edenbaum et al. | |
| 4,781,189 A * | 11/1988 | Vijil-Rosales | 606/192 |
| 5,069,203 A * | 12/1991 | Anderson | 602/21 |
| 5,328,449 A | 7/1994 | Andrews et al. | |
| 5,350,418 A | 9/1994 | Janevski et al. | |
| 5,409,472 A | 4/1995 | Rawlings et al. | |
| 5,558,918 A | 9/1996 | Gordon et al. | |
| 5,643,189 A | 7/1997 | Masini | |
| 5,685,834 A | 11/1997 | Barth | |
| 5,766,142 A * | 6/1998 | Hess | 602/22 |
| 5,833,646 A | 11/1998 | Masini | |

(Continued)

OTHER PUBLICATIONS

MSF Medical Catalogue, vol. 2, 2003, EANE, "BAND, ESMARCH, 6 cm×5 m," 2 pages.

(Continued)

Primary Examiner — Kevin T Truong
(74) Attorney, Agent, or Firm — Woodard, Emhardt, Moriarty, McNett & Henry LLP (57) ABSTRACT A device for exsanguination from the hand and/or arm is described. In one embodiment, the device includes a gripping portion gripped by the hand of a patient holding the device. There is a cupped portion, and a roll of elastic wrapping material. The cupped portion has an inner space for receiving the roll and a slot for feeding out a length of wrap from the roll. The wrap material is fed out of the slot and wrapped around the hand of the patient so that the constrictive force pushes the blood out. A tourniquet is then applied and the wrap removed. In another embodiment, the device has a gripping portion with an end that is slotted to receive and anchor an end of a roll of wrapping material. With an end anchored, the material is unrolled and wrapped from the anchored end down around the hand gripping the device.

9 Claims, 8 Drawing Sheets

U.S. PATENT DOCUMENTS

| | | | |
|---|---|---|---|
| 5,947,915 | A | 9/1999 | Thibodo, Jr. |
| 6,329,564 | B1 | 12/2001 | Lebner |
| 6,482,168 | B1 | 11/2002 | Betcher |
| 6,488,643 | B1 | 12/2002 | Tumey et al. |
| 6,573,419 | B2 | 6/2003 | Naimer |
| 6,664,435 | B2 | 12/2003 | Masini |
| 2002/0193723 | A1 | 12/2002 | Baldorf |
| 2003/0088201 | A1 | 5/2003 | Darcey |
| 2003/0088202 | A1 | 5/2003 | Gilman |
| 2003/0149389 | A1 | 8/2003 | Daneshvar |

OTHER PUBLICATIONS

MEDICA Portal, "New device for Bloodless Surgery of the limbs," Sep. 9, 2003, 2 pages, http://www11.medica.de/cgi-bin/md_medica/custom/pub/content.cgi?lang=2&ticket=g_a_s....

* cited by examiner

EXSANGUNATION DEVICE AND METHOD

CROSS-REFERENCE TO RELATED APPLICATIONS

This application is a National Stage of International Application No. PCT/US2005/017591, filed May 19, 2005 (which was published in English), which is a continuation-in-part of prior U.S. application Ser. No. 10/848,692, filed May 19, 2004 now abandoned, both of which are hereby incorporated by reference in their entirety.

TECHNICAL FIELD

The present device relates to devices to exsanguinate blood from the limbs and more particularly to exsanguinate blood from the hand.

BACKGROUND

Blood commonly needs to be exsanguinated from an area before surgery. A common device to empty venous blood from limbs is an Esmarch band. The device was first introduced in 1870 by Dr. Esmarch, a German physician. The Esmarch band is wrapped around a limb to empty the blood from the limb. Many times the Esmarch band is tied around the end of the limb to act as a tourniquet to complete the exsanguination of the blood from the limb. When exsanguinating blood from the hand, the patient will hold onto something such as a ball of gauze. The hand is then wrapped with the Esmarch band and the gauze helps to keep the fingers spaced apart.

New varieties of devices have been created to exsanguinate blood from the limbs and extremities of a patient. One such device named the S-MART™ has been devised by OHK Medical Devices of Haifa, Israel. S-MART™ consists of a silicone ring, wrapped with a tubular elastic sleeve and a set of pull straps. It is placed on the end of a limb and the straps are pulled. The device rolls over the limbs exerting circumferential pressure draining the blood from the limb. In addition, the sterile sleeve unfolds off of the limb. The ring then creates an arterial block and it stays on for the duration of the operation.

The Esmarch band is relatively inexpensive, easily available, and many medical professionals are comfortable using the Esmarch band. The S-MART™ device is more expensive, not as easily manufactured or available, and has not been around for a long time in contrast to the Esmarch band. The Esmarch band, however, has many limitations, especially when wrapping a hand. First, beginning the wrapping of the band around the limb is awkward. Furthermore, a ball of gauze fails to position the fingers for effective exsanguination of blood.

Therefore, many needs exist in this area of technology.

SUMMARY

One aspect of the invention includes device comprising a gripping member including a gripping portion and an attachment portion, wherein the gripping portion is constructed and arranged to be held by a human hand; and a wrapping material, wherein the wrapping material is operatively coupled to the attachment portion and wrapped around the device and the hand.

Another aspect of the invention includes a method comprising gripping a device with a hand, attaching a wrapping material to the device and wrapping the wrapping material around the device and the hand, wherein the wrapping exsanguinates blood from the hand.

A further aspect of the invention includes a device comprising a gripping member including a core and a grip, the core including a first portion and a second portion, wherein the grip encloses the first portion of the core and is constructed and arranged to be held by a human hand, wherein the second portion of the core defines a slot, and wrapping material, wherein the wrapping material is operatively coupled to the second portion at the slot and wrapped around the hand and the device.

An additional aspect of the invention includes device comprising a core including a first portion and a second portion, wherein the second portion defines a slot that passes through the core; a grip formed around the first portion of the core, wherein the grip defines a frusto-conical shape constructed and arranged to conform to a human hand; and a wrapping material operatively coupled to the second portion and wrapped around the hand and the device.

A further aspect of the invention includes a device for exsanguination comprises: a portion to be gripped by the hand of a patient; a portion coupled to the gripping portion and having an inner area and a slot; and a roll of wrapping material which is received inside the inner area whereby a length of the wrap can be drawn from the roll out through the slot for wrapping the hand.

Yet another aspect of the invention includes a method of exsanguination from an extremity comprises: gripping a gripping portion of an exsanguination device; drawing wrap out of an aperture defined in the exsanguination device; and wrapping the wrap around the device and the extremity, wherein the wrapping of the wrap exsanguinates the hand.

An additional aspect of the invention includes a device for use in exsanguination of a human hand comprises a handle having an external surface sized to accommodate gripping by the hand, and wherein the surface facilitates gripping simultaneously by all fingers of the hand gripping the handle. A roll of flexible strip material for wrapping the hand onto the handle while the hand is gripping the handle is provided from within the handle. A stabilizer is mounted on the handle for stabilizing the roll while the strip material is unrolled from the roll, and a guide slot is incorporated into the handle for controlling the strip as the strip is unrolled from the roll.

The above is not intended to alter the scope of the claims in any way. Any use of this section to alter the scope of the invention as defined in the claims is improper and is not the intention of the drafter. One is directed to the claims at the end of this document, which define the various claimed inventions.

DESCRIPTION OF THE ILLUSTRATED EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations, modifications, and further applications of the principles of the present invention as illustrated being contemplated as would normally occur to one skilled in the art to which the invention relates.

Figure 1:
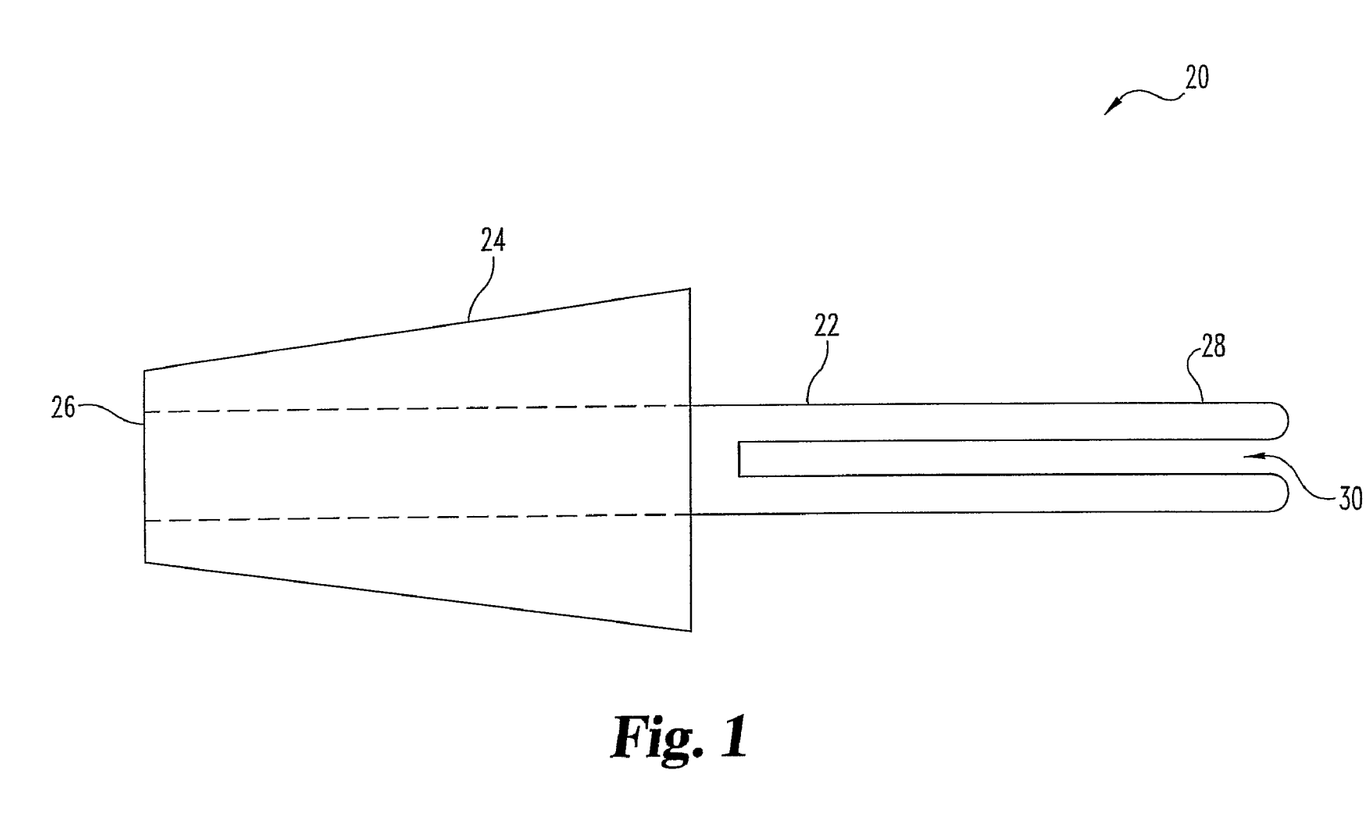
FIG. 1 illustrates a side view of one embodiment of the present invention.

In FIG. 1, an exsanguination device 20 according to one embodiment is illustrated. The exsanguination device 20 is a gripping member including a core 22 to provide a solid base that the grip 24 may be wrapped around. The grip 24 is coupled to the core 22. The coupling is achieved through a variety of methods. For example, an epoxy or adhesive may be used to couple the core 22 and the grip 24. Alternatively in other embodiments, the core 22 may be formed of two symmetrical pieces that collapse around a section of the grip 24 to firmly bind them together. Alternate embodiments contemplate a core 22 and a grip 24 that are a one piece gripping member. Moreover, other embodiments readily apparent to those skilled in the art for combining the grip 24 and the core 22 are contemplated.

In the illustrated embodiment, the core 22 is composed of a durable high-strength plastic. In alternative embodiments, it is contemplated that the core 22 is formed of different materials. One example, among others, would be a core 22 that is formed of a metallic material. In the illustrated embodiment, the core 22 defines a cylindrical shape. In other embodiments, the core 22 may have a different cross sectional shape. For example, in an alternate embodiment, the core 22 has a square shaped cross-section. In the illustrated embodiment, the core 22 has about 70% of its surface area covered by the grip 24. Alternate embodiments contemplate the grip 24 covering more or less of the surface area of the core 22.

The core 22 includes a first portion 26 covered by the grip 24 to create a gripping portion of the core 22, and a second portion 28 that defines a slot 30. In the illustrated embodiment, the slot 30 is used to attach wrapping material (not shown) to the second portion 28. The second portion 28 is the attachment portion in the illustrated embodiment. Other attachment means may be used for the second portion 28 in other embodiments. For example, one alternate embodiment includes a clip that firmly grips the wrapping material (not shown). Moreover, other embodiments have alternate methods readily apparent to those skilled in the art for attaching wrapping material (not shown) to the second portion 28. In addition, in alternate embodiments, the second portion 28 defines multiple slots. Moreover, in the illustrated embodiment, the second portion 28 is serrated. Alternate embodiments have other methods of texturing the second portion 28. For example, alternate embodiments may have ridges, grooves, bumps, cones, spikes or other texturing constructions to enable a secure connection between the second portion 28 and the wrapping material (not shown).

In the illustrated embodiment, the grip 24 defines a frusto-conical shape. The frustoconical shape is utilized so that a human hand can be comfortably wrapped around the grip 24. Moreover, the frusto-conical shape will conform to different sized human hands. For example, a human with a small hand is able to firmly wrap their hand around the section of the grip 24 that covers the first portion 26 of the core 22. A human with a large hand will be able to firmly wrap their hand around the section of the grip 24 that is closer to the second portion 28 of the core 22. The grip 24 therefore encourages positioning the hand and fingers of all sizes for effective blood exsanguination. In the illustrated embodiment, the angle of incline of the frusto-conical shape from the part of the grip 24 covering the first portion 26 of the core 22 towards the second portion 28 of the core 22 is small. Other embodiments contemplate a steeper angle of incline. In the illustrated embodiment, the grip 24 has a maximum diameter of about two inches and a minimum diameter of about one and a half inches. The length of the grip 24 is about six and one half inches in length. One non-limiting example of an embodiment with different dimensions is an exsanguination device 20 having a grip that is only five inches in length. Furthermore, other embodiments contemplate different shapes that conform to the human hand, such as a cone or cylinder.

In the illustrated embodiment, the grip 24 is composed of a resilient foam material. In some embodiments, Rebond or Evazote type foam is used. Other embodiments contemplate using other types of foam materials. Preferably, an impact-resistant durable foam is used. Moreover, other materials readily apparent to those skilled in the art are utilized in alternate embodiments. Generally, enclosing the core 22 with a spongy-type material allows a firm, comfortable and secure grip of the exsanguination device 20. The spongy-type material also prevents the wrapping of the hand from being more uncomfortable than necessary. In some alternate embodiments, the grip 24 is textured.

Figure 2:
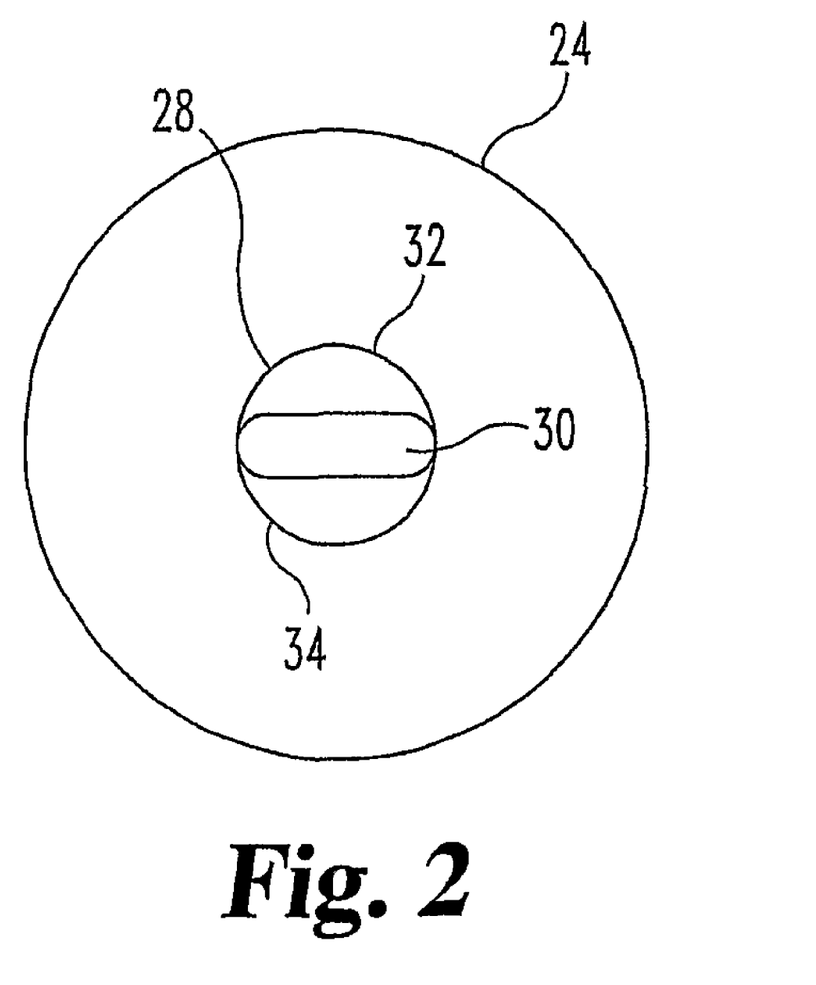
FIG. 2 is an end view of the device illustrated in FIG. 1.

Referring now to FIG. 2, an end view of the device of FIG. 1 looking down the second portion 28 is illustrated. The end view illustrates that the slot 30 separates the second portion 28 of the core 22 into a first prong 32 and a second prong 34. The prongs 32, 34 provide an area that the wrapping material (not shown) may be tied around. The view of FIG. 2 illustrates that the grip 24 is at its maximum diameter towards the second portion 28. Travelling towards the first portion 26 the diameter of the grip 24 gradually decreases along the length of the core 22. This defines the frusto-conical shape of the grip 24 illustrated in FIGS. 1 and 2.

Figure 3:
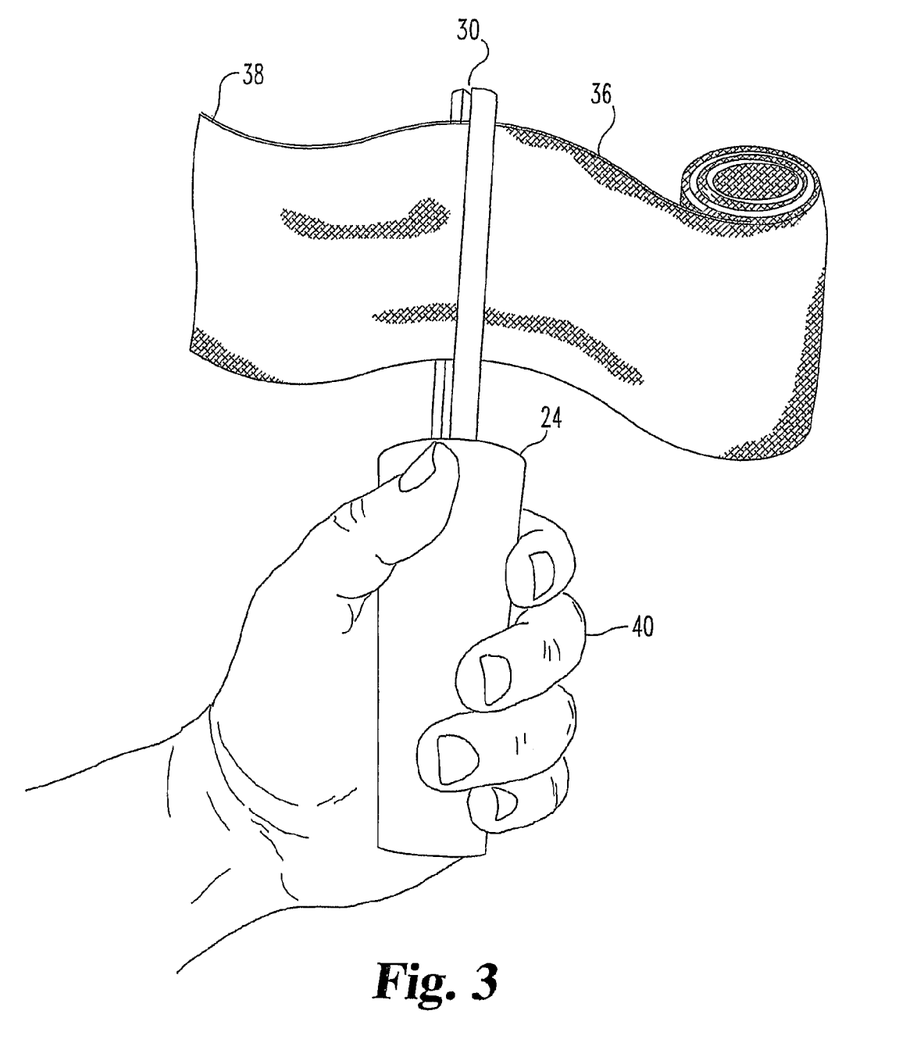
FIG. 3 is a perspective view of the device illustrated in FIG. 1 beginning with the wrapping of the user's hand.

FIG. 3 illustrates the device of FIG. 1 during use of the device prior to surgery. Wrapping material 36 having a first end 38 is passed through slot 30 to begin the attachment of the wrapping material 36 to the exsanguination device 20. The patient's hand 40 grips the grip 24. The frusto-conical shape of the grip 24 conforms to the size of the hand. Moreover, the shape of the grip 24 helps to spread the fingers and hand apart thereby allowing an easier and more complete wrapping of the hand. Spreading the fingers apart enables effective exsanguination of blood. For example, the patient using the illustrated embodiment has extended the thumb vertically to further assist in the exsanguination of blood from the thumb.

The wrapping material 36 may be an Esmarch band or similar type wrap. The wrapping material is generally flexible and elastic so that it may be stretched to apply a compressive force to the hand to exsanguinate the blood out of the hand.

Figure 4:
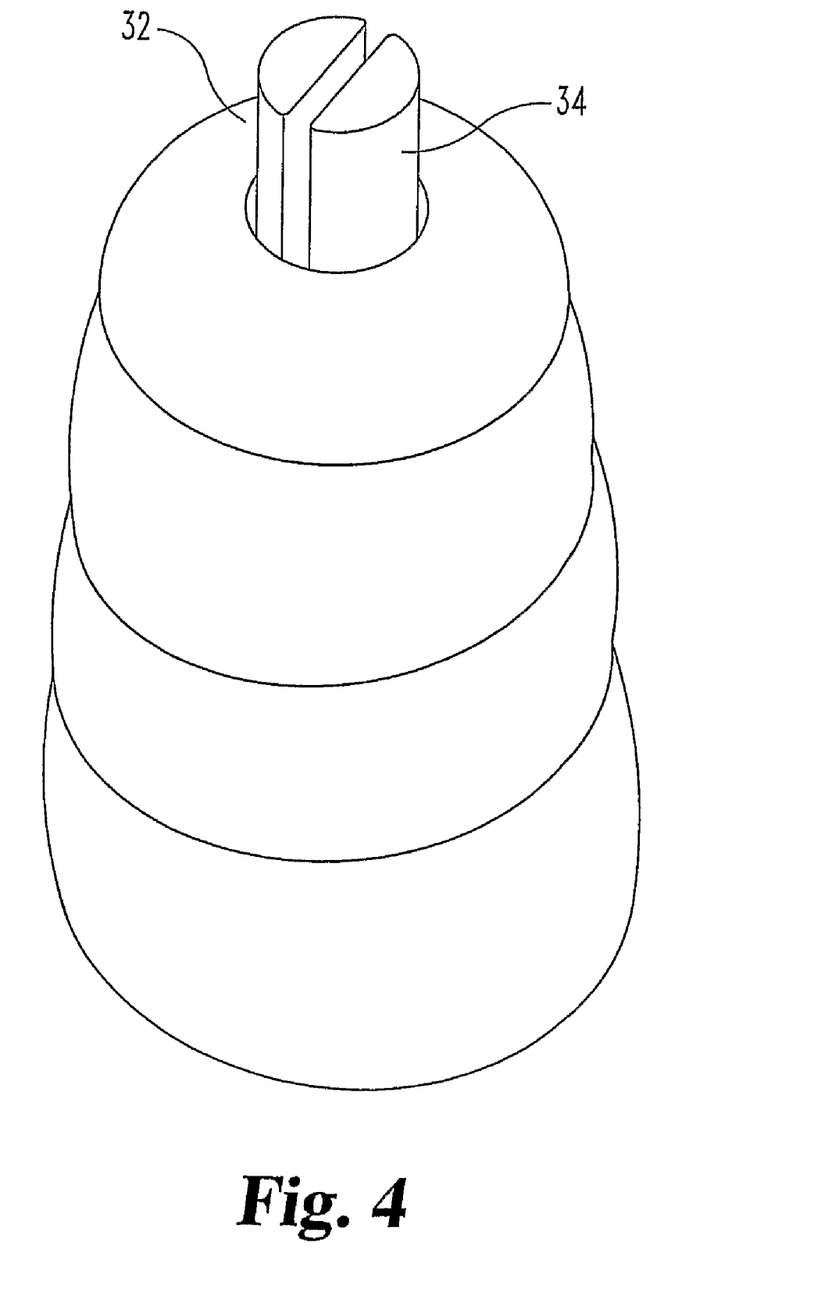
FIG. 4 is a perspective view of the device of FIG. 1 after the hand and device has been wrapped.

The wrapping material is attached to the exsanguination device 20 at the second portion 28 and wrapped around the exsanguination device 20 in a spiral pattern in order to enclose the hand and the exsanguination device 20 within the wrapping material 36. As illustrated in FIG. 4, after the wrapping material 36 has been applied a "bee hive" type shape is created around the patient's hand. Only the patient's wrist extends from the bottom. The wrap exsanguinates the blood from the hand so bloodless surgery may be performed on the hand. In addition, a local block is generally applied to the hand using an anesthetic to prevent the patient from experiencing pain during surgery.

Figure 5:
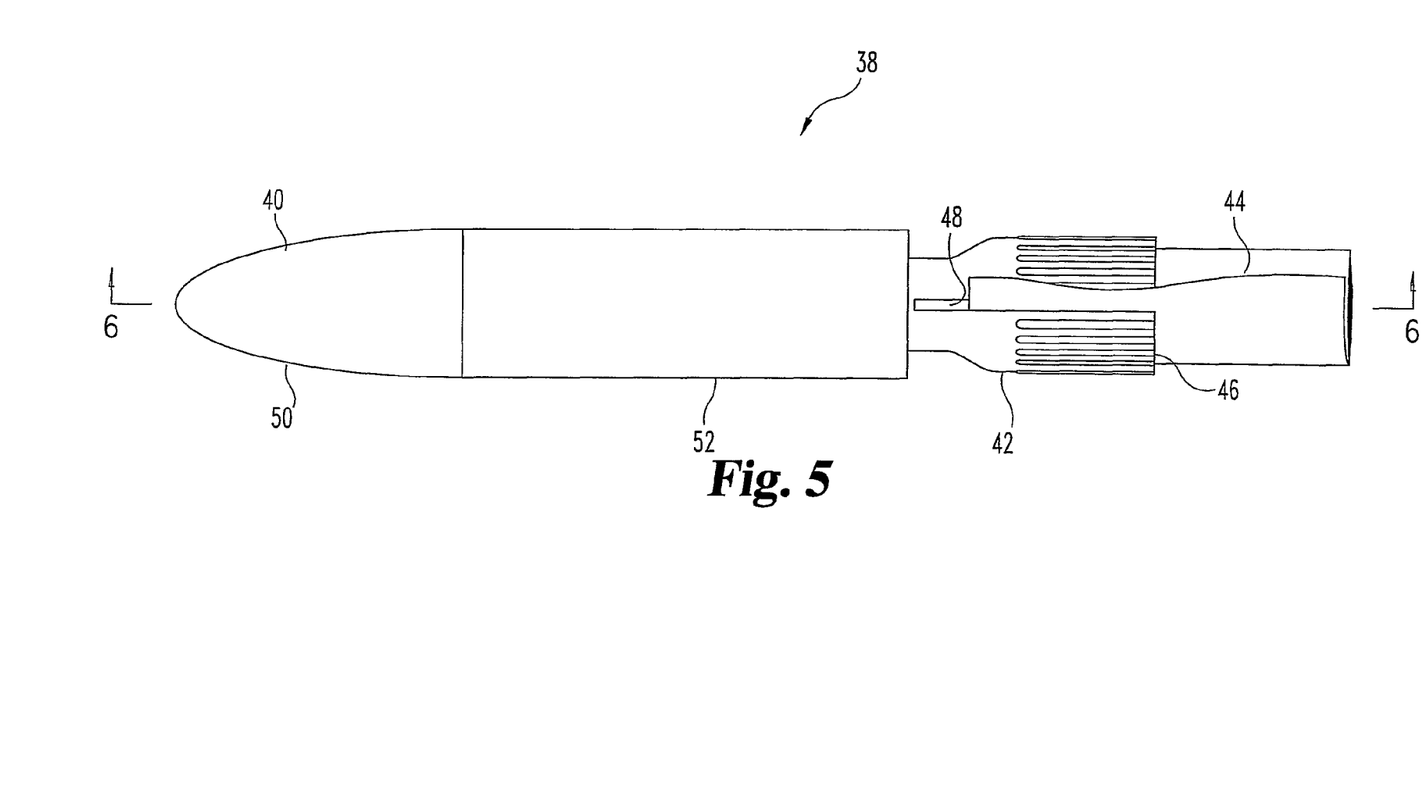
FIG. 5 is a side view of another embodiment of the present invention.

Referring now to FIG. 5, a second embodiment of an exsanguination device 38 is illustrated. The exsanguination device 38 generally includes a gripping portion 40 and a cupped portion 42, and a roll 44 of wrap. The device 38 is generally cylindrical and rounded at one end. The cupped portion 42 is open at one end and at the other end and has an inner space 46 for receiving the roll 44. The cupped portion 42 also has a slot 48 that receives the end of the roll 44 to be threaded through the slot 48 to assist in dispensing the wrap during use. The slot 48 guides the unrolling of the roll 44 of wrap.

The gripping portion 40 is formed from the combination of a first part 50 and a second part 52. The two parts 50 and 52 are generally constructed and arranged to be comfortably gripped and held in the patient's hand which is to be wrapped. The first part has a generally parabaloid shape. The second part 52 has a cylindrical shape. The first part 50 and the second part 52 are generally formed of a resilient material, such as foam or the like. The size of the illustrated embodiment is, for example but not limited to, a first part 50 that is about three inches in length, a second part 52 that is about four and three-quarter inches in length and 1.5 inches outside diameter, a cupped portion 42 that is about two inches in length and 1.5 inches inside diameter.

In the illustrated example, the roll 44 is formed of wrap material strip four inches wide that is rolled up into a roll about 1.4 inches in diameter and four inches long. The roll can be supplied without or with a core or spool. In the illustrated embodiment, the four inch roll is received in a cupped portion 42 that is about two inches in height. The interior walls of the cupped portion 42 are a stabilizer for the unrolling of the roll 44. In other embodiments, the roll 44 can be received in different ways. For one example, but not intended to be limiting, the cupped portion 42 could have a closed or pop-top that encloses an inner space 46 where the roll 44 is completely enclosed inside. The wrap can be an Esmarch band or similar type wrap. The wrap is flexible and generally elastic so that it may be stretched to apply a compressive force throughout to exsanguinate the hand. In certain circumstances, the device may be used with a wrap that is made of fabric or other non-rubber-like material.

Figure 6:
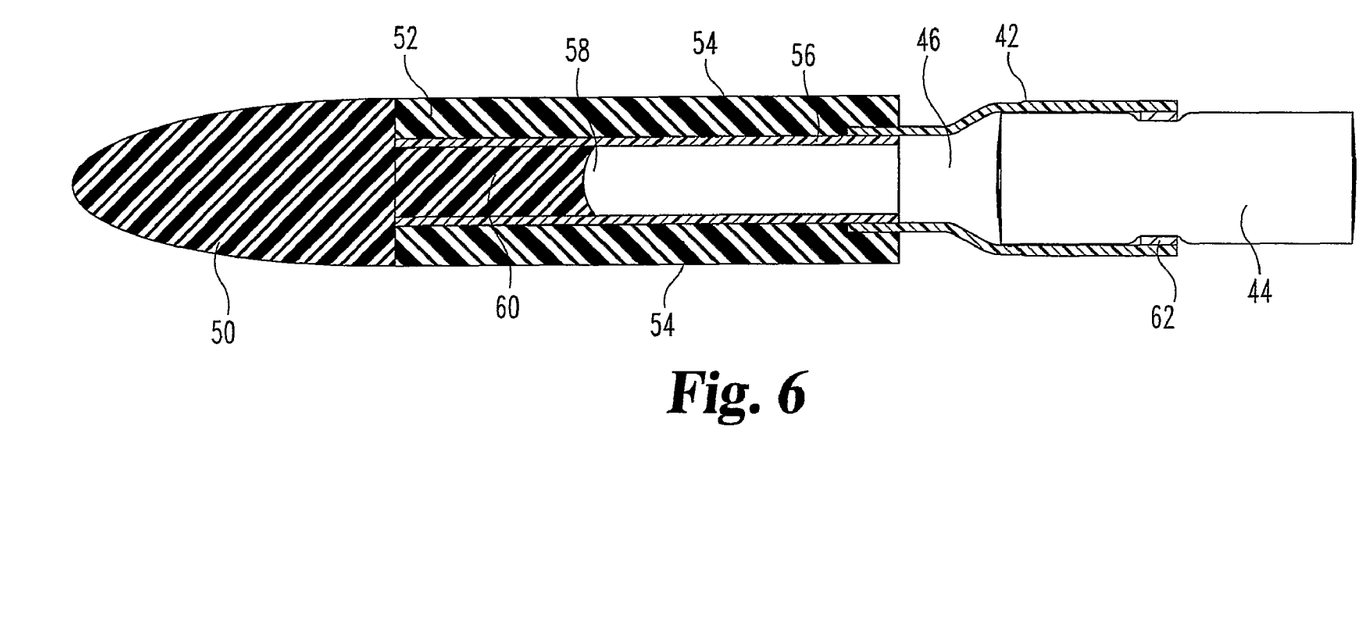
FIG. 6 is a sectional view of the embodiment illustrated in FIG. 5 taken at line 6-6 and viewed in the direction of the arrows.

FIG. 6 illustrates that the first part 50 is solid throughout. The second part 52 is generally shown to be composed of several layers and spaces. The outermost layer is the sleeve 54 that is glued to end piece 50 and provides a resilient surface for comfortable gripping by the patient's hand spreading the fingers when in use. For this purpose, the sleeve 54, like end piece 50, may be composed of a foam-like material, for example. The internal core of the second part 52 includes a tube 56 of harder plastic material that lends structural stability to the exsanguination device 38. A pillar 60 of material, such as foam, is glued to end piece 50 and is received in the tube interior space 58. As such, it cooperates with sleeve 54 to be friction fitted to the tube 56 and holds the parts 50 and 52 to the tube 56. The cupped portion 42, also of a plastic like that of tube 56, is received and fixed to an end of the tube 56 to provide a smooth transition from the tube 56 to the cupped portion 42. The cupped portion 42 also includes an inner lip 62 to assist in holding the roll 44 in place.

The second embodiment of the exsanguination device 38 operates as follows. A roll 44 of wrap material is placed into the inner space 46 through the open end of the cupped portion 42. The patient grips the exsanguinations device 38 such as shown in FIG. 7, for example.

The medical professional then begins to draw wrap out of the roll 44 through the slot 48 and around the patient's hand gripping the device. The wrapping can be continued to wrap around a portion of the patient's arm depending upon the extent needed for a subsequent surgical procedure to be done. The wrap feeds out of the slot 48 by the rotation of the roll 44 as it unwinds. When the needed wrapping and exsanguination has been completed, the medical professional will apply a tourniquet where the wrap terminated. The tourniquet can be a separate device from the wrap, or a section of the unused wrap can be used to form the tourniquet. After the tourniquet has been applied, then the wrap can be removed from the patient's hand and the exsanguinations device removed, and surgical procedure begun.

Generally elongate shapes for the device, other than the paraboloid and cylindrical combination shown, and which can be gripped with a hand relatively open for exsanguinations, are contemplated. In addition, in alternative embodiments, other materials besides foam can be used. For example, but not limited to, a polymer, other plastics, fabric, animal hide, rubber, wood, or metal can be used to form the sleeve 54 or the first part 50. In addition, the level of compressibility, if any, of the gripped surfaces may vary in different embodiments. In most cases, some cushioning of the hand on the gripped surface is preferable.

Figure 7:
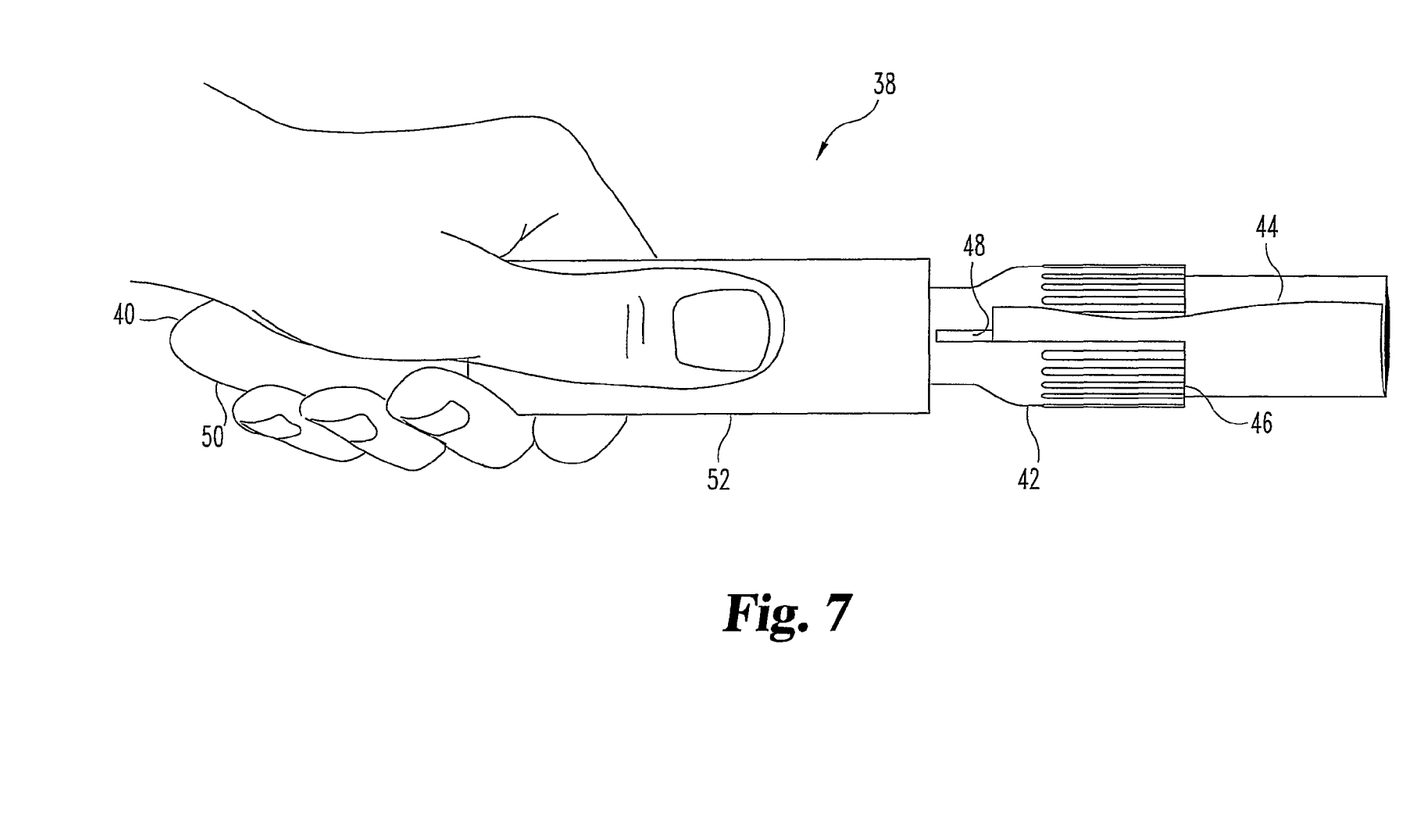
FIG. 7 is a perspective view of the device of FIGS. 5 and 6 being held in a hand ready for wrapping.
Figure 8:
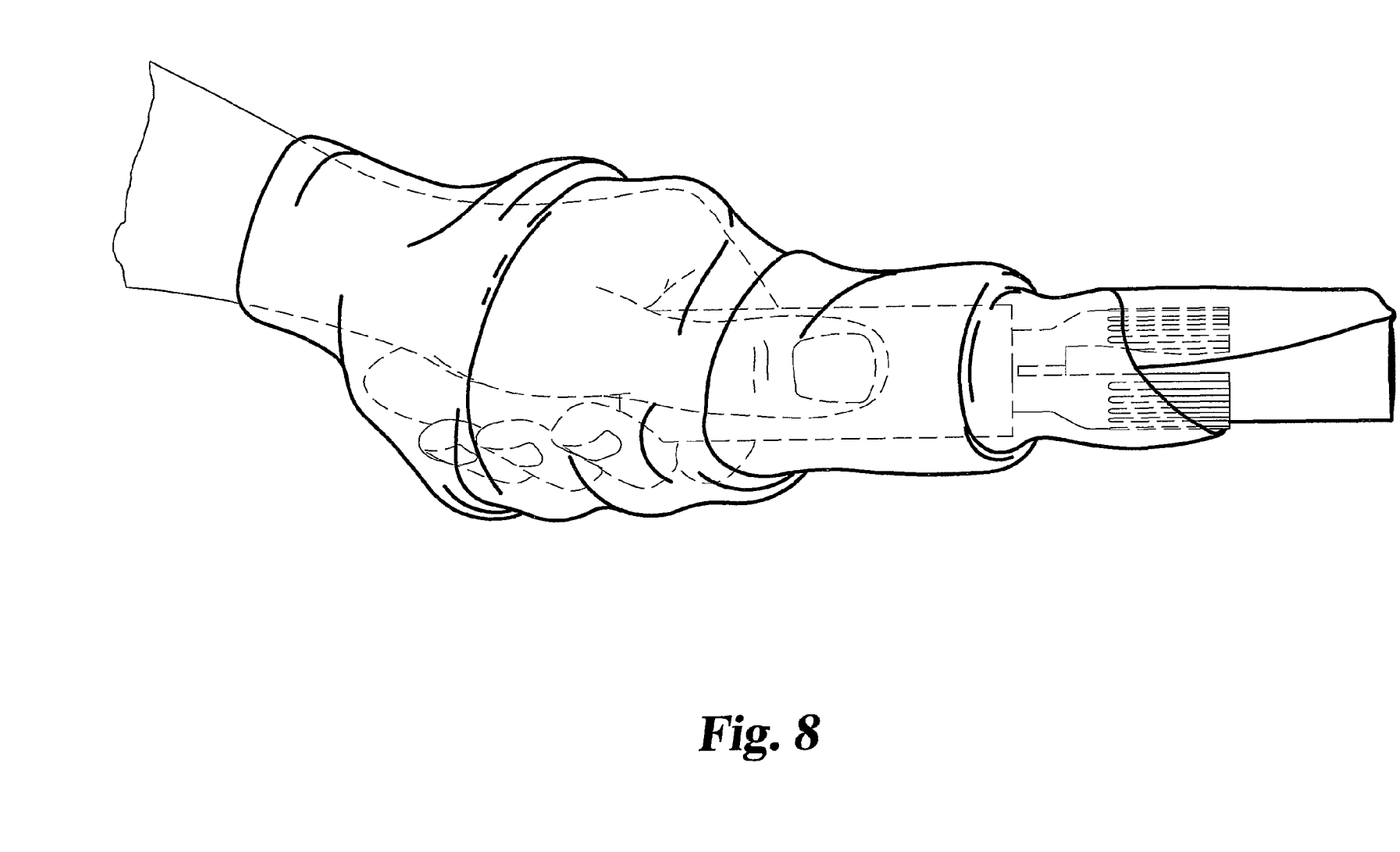
FIG. 8 is a perspective view of the device of FIGS. 5-7 wrapping the hand.

FIG. 8 illustrates the device and hand of FIG. 7 completely wrapped. The compressive forces of the wrap squeeze the fluid out of the hand. A tourniquet can be applied to ensure that the hand stays bloodless during surgery.

Moreover, other possible embodiments are contemplated. For example, a pin (not shown) can be provided through the center of the roll 44 with the wrap wound around the pin. The pin can extend into the interior of the second part 52 and be received in a socket in part 52 for rotation therein. If the roll is mounted on a spool, with a hole in the spool, the pin can be fixed in part 52 for the spool to rotate on the pin as the wrap is pulled out through the slot 48. In these examples, the pin or pinned spool provides a stabilizer for the roll.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A method of exsanguination of an extremity comprising:
 gripping with said extremity, a gripping portion of an exsanguination device;
 while the extremity is gripping the gripping portion, drawing a wrapping material from storage through an exit defined in the exsanguination device; and
 wrapping the wrapping material around a portion of the device and the extremity; whereby the wrapping exsanguinates the extremity; supporting a quantity of the wrapping material on the exsanguination device as the device is gripped by the hand being wrapped, and wherein said wrapping draws said wrapping material from said quantity through said exit; and said wrapping is done around said hand and device whereby exsanguination of said hand occurs.

2. A method, comprising:
 providing an exsanguination device having a gripping portion, a holder portion coupled to the gripping portion and having a dispensing slot, and a roll of wrapping material received by the holder portion;

gripping the gripping portion of the exsanguination device with a hand;

pulling a portion of the wrapping material out of the holder portion through the slot; and exsanguinating blood from the hand, wherein the exsanguinating includes tightly wrapping the portion of wrapping material around the device and the hand.

3. A method, comprising:

providing an exsanguination device having a gripping portion, a dispensing portion, and a quantity of wrapping material received by the dispensing portion;

gripping the gripping portion of the exsanguination device with a hand;

dispensing the wrapping material from the dispensing portion; and tightly wrapping the wrapping material around the device and the hand, whereby the wrapping causes exsanguination of blood from the hand.

4. The method of claim 3, wherein the dispensing portion defines an inner space and a slot in communication with the inner space, wherein the wrapping material is positioned in the inner space, and wherein the dispensing includes pulling the wrapping material through the slot.

5. The method of claim 4, wherein the dispensing portion includes an open end in communication with the inner space to enable insertion of the quantity of wrapping material into the inner space.

6. The method of claim 3, wherein the quantity of wrapping material is a roll of flexible, elastic wrapping material.

7. The method of claim 3, wherein the gripping portion includes a foam grip surrounding a core.

8. The method of claim 3, wherein the gripping portion includes a first end portion being parabaloid in shape and a second portion adjacent the first portion, the second portion being cylindrical in shape.

9. The method of claim 3, wherein the wrapping material is a stretchable, flexible, elastic wrap operable to apply a compressive force to the hand.

* * * * *

UNITED STATES PATENT AND TRADEMARK OFFICE
CERTIFICATE OF CORRECTION

PATENT NO. : 7,942,841 B2  
APPLICATION NO. : 11/569296  
DATED : May 17, 2011  
INVENTOR(S) : Chester Y. Sakura, Jr.

Page 1 of 1

It is certified that error appears in the above-identified patent and that said Letters Patent is hereby corrected as shown below:

Patent Title page, item (54) and col. 1, line 1; title, replace "EXSANGUNATION" with
-- EXSANGUINATION --

Signed and Sealed this
Twelfth Day of July, 2011

David J. Kappos
*Director of the United States Patent and Trademark Office*